(12) United States Patent
Kim et al.

(10) Patent No.: US 10,312,215 B2
(45) Date of Patent: Jun. 4, 2019

(54) ELECTRODE ASSEMBLY AND METHOD FOR MANUFACTURING SAME

(71) Applicant: Electronics and Telecommunications Research Institute, Daejeon (KR)

(72) Inventors: Yong Hee Kim, Daejeon (KR); Sang Don Jung, Daejeon (KR)

(73) Assignee: ELECTRONICS AND TELECOMMUNICATIONS RESEARCH INSTIT, Daejeon (KR)

( * ) Notice: Subject to any disclaimer, the term of this patent is extended or adjusted under 35 U.S.C. 154(b) by 0 days.

(21) Appl. No.: 15/445,549

(22) Filed: Feb. 28, 2017

(65) Prior Publication Data

US 2017/0250157 A1    Aug. 31, 2017

(30) Foreign Application Priority Data

Feb. 29, 2016    (KR) .......................... 10-2016-0024374

(51) Int. Cl.
*H01L 23/48*    (2006.01)
*H01L 23/00*    (2006.01)
(Continued)

(52) U.S. Cl.
CPC ............ *H01L 24/81* (2013.01); *A61B 5/0031* (2013.01); *A61B 5/686* (2013.01); *A61N 1/0472* (2013.01); *A61N 1/05* (2013.01); *H01L 21/2636* (2013.01); *H01L 21/76879* (2013.01); *H01L 21/76898* (2013.01); *H01L 23/481* (2013.01); *H01L 24/13* (2013.01); *A61B 2562/0209* (2013.01); *A61B 2562/125* (2013.01)

(58) Field of Classification Search
CPC ................. H01L 24/81; H01L 21/2636; H01L 21/76879; H01L 21/76898; H01L 23/481; H01L 24/13; A61N 1/04; G02F 1/133; G06F 1/1652; G06F 3/044
See application file for complete search history.

(56) References Cited

U.S. PATENT DOCUMENTS 5,233,152 A * 8/1993 Prokosch ............. B23K 1/0056
                                                    219/121.63
8,404,388 B2 * 3/2013 Visco ..................... H01B 1/122
                                                    429/231.9
(Continued)

FOREIGN PATENT DOCUMENTS

KR    10-2008-0033820 A    4/2008
KR    10-2015-0095964 A    8/2015
KR    10-2015-0109032 A    10/2015

OTHER PUBLICATIONS

John D. Yeager et al., "Microstructual characterization of thin gold films on a polyimide substrate", Thin Solid Films, May 19, 2010, pp. 5896-5900, 518, ELSEVIER B. V.
(Continued)

*Primary Examiner* — Victor A Mandala
*Assistant Examiner* — Colleen E Snow (57) ABSTRACT

Provided is an electrode assembly which may be manufactured by providing a first substrate and a second substrate, plasma treating the first substrate, forming an electrode on the first substrate, and thermally compressing the first substrate and the second substrate, with the electrode therebetween, wherein each of the first substrate and the second substrate includes a fluorine-based polymer.

9 Claims, 10 Drawing Sheets

(51) Int. Cl.
    *H01L 21/263*     (2006.01)
    *H01L 21/768*     (2006.01)
    *A61B 5/00*     (2006.01)
    *A61N 1/05*     (2006.01)
    *A61N 1/04*     (2006.01)

(56) References Cited

U.S. PATENT DOCUMENTS

| | | |
|---|---|---|
| 2013/0033671 A1 | 2/2013 | Schadt et al. |
| 2014/0020936 A1 | 1/2014 | Kim et al. |
| 2015/0112180 A1 | 4/2015 | Kim et al. |
| 2016/0362791 A1* | 12/2016 | Yamamura .............. C23C 18/04 |
| 2017/0040582 A1* | 2/2017 | Kim .................... H01M 2/1061 |

OTHER PUBLICATIONS

Takayuki Komori et al., "Fabrication of Au micro-electrodes on polyimide films using transfer printing techniques", Applied Mechanics and Materials, Feb. 13, 2013, pp. 1368-1371, 300-301, Trans Tech Publications.

Alan K. Mo et al., "Understanding the Mechanism of Solvent-Mediated Adhesion of Vacuum Deposited Au and Pt Thin Films onto PMMA Substrates", Advanced Functional Materials, Oct. 18, 2012, pp. 1431-1439, 23, Wiley-VCH Verlagg GmbH & Co. KGaA, Weinheim.

Ikjoo Byun et al., "Transfer of thin Au films to polydimethylsiloxane (PDMS) with reliable bonding using (3-mercaptopropyl)trimethoxysilane (MPTMS) as a molecular adhesive", J. Micromech. Microeng. Jul. 3, 2013, pp. 1-10, 23, IOP Publishing.

\* cited by examiner

ELECTRODE ASSEMBLY AND METHOD FOR MANUFACTURING SAME

CROSS-REFERENCE TO RELATED APPLICATIONS

This U.S. non-provisional patent application claims priority under 35 U.S.C. § 119 of Korean Patent Application No. 10-2016-0024374, filed on Feb. 29, 2016, the entire contents of which are hereby incorporated by reference.

BACKGROUND

The present disclosure herein relates to an electrode assembly and a method for manufacturing the same, and more particularly, to an electrode assembly including a plasma surface-treated fluorine-based polymer substrate, and a method for manufacturing the same.

Polymer film-metal assemblies have both the flexibility of polymers and the electrical conductivity of metals. Thus, such polymer film-metal assemblies are used in various applications such as bio-implantable, wearable, or bio-attachable elements and systems, flexible touch screens, and metal corrosion prevention.

Stable metals such as gold (Au) and platinum (Pt) have the disadvantage of having weak bonding strength, and thus of being easily detached, when attached to polymers. Thus, typically, in order to increase the adhesion strength between a metal such as gold (Au) and platinum (Pt), and a polymer, an adhesive layer, composed of chrome (Cr) or titanium (Ti) and the like, having relatively good adhesion strength with polymers is interposed between the metal and the polymer.

However, assemblies that utilize an adhesive layer composed of chrome (Cr) or titanium (Ti) and the like have the limitation of being corroded or having weakened adhesion strength when used for extended periods of time, due to bodily fluids, sweat, moisture, or repeated mechanical stimulation, etc. Moreover, ultimately, the metal such as gold (Au) or platinum (Pt) and the like is delaminated from the polymer film. In particular, the adhesive layer is ineffective for fluorine-based polymers having low surface energy, and thus such fluorine-based polymers are characterized in having inherently weak bonding with metals.

SUMMARY

The present disclosure provides an electrode assembly having increased adhesion strength between a substrate and an electrode, and a method for manufacturing the same.

An embodiment of the inventive concept provides a method for manufacturing an electrode assembly, the method including providing a first substrate and a second substrate; plasma treating the first substrate; forming an electrode on the first substrate; and thermally compressing the first substrate and the second substrate, with the electrode therebetween, wherein each of the first substrate and the second substrate includes a fluorine-based polymer.

In an embodiment, the fluorine-based polymer may include at least one among polychlorotrifluoroethylene (PCTFE), perfluoro-2,2-dimethyl-1,3-dioxide (PDD), chlorotrifluoroethylene (CTFE), perfluoro-3-butenyl-vinylether (PBVE), perfluoropropylvinylether (PPVE), polytetrafluoroethylene (PTFE), polyvinylidenefluoride (PVDF), polyvinylfluoride (PVF), vinylidene fluoride (VDF), a PBVE-based homopolymer (Cytop™), and a copolymer including at least two thereof.

In an embodiment, the copolymer may be a copolymer of ethylene and CTFE (ECTFE), a copolymer of ethylene and TFE (ETFE), a copolymer of fluorinated ethylene and propylene (FEP), hexafluoropropylene (HFP), a copolymer of TFE and PPVE (PFA), a copolymer of TFE and PDD (Teflon™ AF), tetrafluoroethylene (TFE), or poly(TFE-co-HFP-co-VDF) (THV).

In an embodiment, the second substrate may also be plasma treated. Mutually facing faces of the first substrate and the second substrate may be plasma treated. In the plasma treatment, the plasma gas may be at least one of argon, helium, oxygen, nitrogen, air, or tetrafluoromethane. The plasma treatment may be performed using one of RF plasma, DC plasma, remote plasma, or magnetron plasma.

In an embodiment, the temperature at which the thermal compression takes place may be between the glass transition temperature and the melting point of the first and second substrates.

In an embodiment, patterning a portion of the second substrate to thereby form a through-hole that exposes a portion of the top face of the electrode may be further included. The patterning of a portion of the second substrate may include forming a protective layer on the top face of the second substrate; patterning the protective layer to thereby remove a first region; etching the second substrate corresponding to a patterned and removed portion of the protective layer; and removing the protective layer. In an embodiment, forming a contact part in the through-hole may be further included, wherein the contact part is composed of a porous conductive material. The contact part may be formed by using an electro-deposition method.

In an embodiment, the first substrate may be heat treated prior to the plasma treatment.

In an embodiment, the electrode may include at least one of gold, silver, or platinum.

In an embodiment, the first and second substrates may be flexible.

In an embodiment of the inventive concept, an electrode assembly manufactured using the method described above may include a first substrate; an electrode provided on the first substrate; and a second substrate which is thermally compressed to the first substrate, with the electrode therebetween. Each of the first substrate and the second substrate may include a fluorine-based polymer.

DETAILED DESCRIPTION

The present invention may be modified in various ways and be embodied in various forms. Hereinafter, specific embodiments of the present invention are described in detail with reference to exemplary drawings. However, such embodiments are not intended to limit the present invention to any particular forms. Rather, the present invention should be construed as including all modifications, equivalents, or substitutes within the spirit and technical scope of the invention.

In describing the respective figures, like reference numerals refer to like elements. In the drawings, the dimensions of structures are exaggerated for clarity of illustration. It will be understood that, although the terms first, second, etc. may be used herein to describe various elements, the elements should not be limited by these terms. These terms are only used to distinguish one element from another element. For example, a first element could be termed a second element, and similarly, a second element could be termed a first element without departing from the scope of the present invention. Singular forms are intended to include the plural forms as well, unless the context clearly indicates otherwise.

In the specification, the terms "includes" or "has" specify the presence of stated features, integers, steps, operations, elements, components, or combinations thereof, but do not preclude the presence or addition of one or more other features, integers, steps, operations, elements, components, or combinations thereof. Moreover, it will be understood that when a part, such as a layer, film, region, plate, etc., is referred to as being "on" another part, it can be "directly above" the other part, or intervening parts may also be present. Furthermore, when a part, such as a layer, film, region, plate, etc., is referred to as being formed "on" another part, the part is not limited to being formed spatially above the other part, but rather, may be formed to the side or below the other part. When a part, such as a layer, film, region, plate, etc., is referred to as being "below" another part, it can be "directly below" the other part, or intervening parts may also be present.

Hereinafter, exemplary embodiments of the inventive concept will be described in detail with reference to the accompanying drawings.

Figure 1:
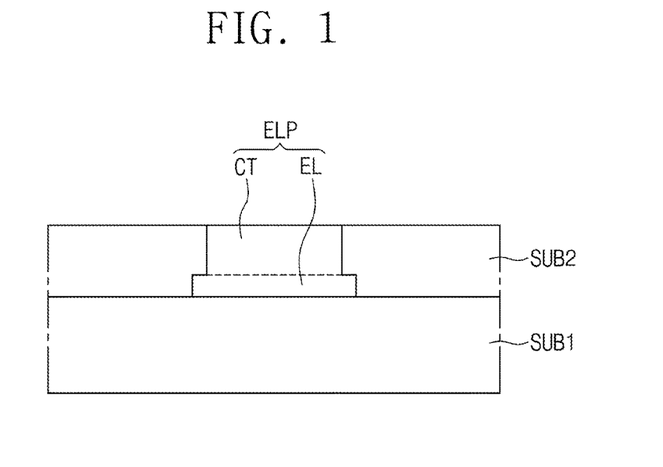
FIG. 1 is a cross-sectional view illustrating an electrode assembly according to an embodiment of the inventive concept.

FIG. 1 is a cross-sectional view illustrating an electrode assembly according to an embodiment of the inventive concept.

An electrode assembly according to an embodiment of the inventive concept is for application to electrodes in various elements, and in particular, for application to elements that require a stable electrode having high resistance to corrosion. The electrode assembly according to an embodiment of the inventive concept may be used in various electronic elements, for example, touch sensors, elements for flexible displays, medical elements, etc. In particular, such medical elements to which the electrode assembly may be applied include all elements that are bio-implantable, bio-attachable, or wearable. In an embodiment of the inventive concept, the electrode assembly is exemplarily described as a neural electrode used inside the human body. However, the field in which the electrode assembly according to an embodiment of the inventive concept is used is not limited thereto, and the electrode assembly may obviously be utilized in various elements.

Referring to FIG. 1, an electrode assembly according to an embodiment of the inventive concept includes a first substrate SUB1, an electrode EL provided on the first substrate SUB1, and a second substrate SUB2 which is thermally compressed to the first substrate SUB2, with the electrode EL thereinbetween.

The electrode EL is mounted on the first substrate SUB1. The first substrate SUB1 may be transparent or opaque. The first substrate SUB1 may be flexible. The first substrate SUB1 may be composed of a polymer insulator.

The polymer insulator may include, in particular, a biostable material. The polymer insulator may include a fluorine-based polymer. The fluorine-based polymer may be less reactive and more stable than typical polymer insulators such as polyimide or poly epoxy and the like. The fluorine-based polymer may have excellent electrical conductivity and chemical resistance, absorbs very little moisture, and is also highly biocompatible. Due to such reasons, the fluorine-based polymer may be appropriate for substrates in bio-implantable electrode assemblies.

The fluorine-based polymer may include at least one among polychlorotrifluoroethylene (PCTFE), perfluoro-2,2-dimethyl-1,3-dioxide (PDD), chlorotrifluoroethylene (CTFE), perfluoro-3-butenyl-vinylether (PBVE), perfluoro-propylvinylether (PPVE), polytetrafluoroethylene (PTFE), polyvinylidenefluoride (PVDF), polyvinylfluoride (PVF), vinylidene fluoride (VDF), a PBVE-based homopolymer (Cytop™), and a copolymer including at least two thereof.

The copolymer may include at least one among a copolymer of ethylene and CTFE (ECTFE), a copolymer of ethylene and TFE (ETFE), a copolymer of fluorinated ethylene and propylene (FEP), hexafluoropropylene (HFP), a copolymer of TFE and PPVE (PFA), a copolymer of TFE and PDD (Teflon™ AF), tetrafluoroethylene (TFE), and poly(TFE-co-HFP-co-VDF) (THV).

The electrode EL may be attached with a high adhesion strength onto the first substrate SUB1.

The electrode EL may include a conductive material. The conductive material may be selected from among highly conductive materials that do not cause problems, even when used inside or in contact with the body.

In an embodiment of the inventive concept, the conductive material may be at least one of gold, silver, may be platinum, and the conductive material may specifically be gold. However, the conductive material is not limited thereto and may be composed of various materials depending on the usage of the electrode assembly. For example, the electrode assembly may include various other conductive materials when used in a touch sensor or the like, and may include various metals, metal alloys, metal oxides, conductive polymers, or nano-conductive materials, etc. In to an embodiment of the inventive concept, the metal may be copper, silver, gold, platinum, palladium, nickel, tin, aluminum, cobalt, rhodium, iridium, iron, ruthenium, osmium, manganese, molybdenum, tungsten, niobium, tantalum, titanium, bismuth, antimony, or lead, etc. The conductive polymer may be a polythiophene-based, polypyrrole-based, polyaniline-based, polyacetylene-based, or polyphenylene-based compound, or mixtures thereof, and in particular, among polythiophene-based compounds, a PEDOT/PSS compound may be used. The conductive metal oxide may be indium tin oxide (ITO), indium zinc oxide (IZO), antimony zinc oxide (AZO), indium tin zinc oxide (ITZO), zinc oxide (ZnO), or tin oxide (SnO2), etc. In addition, the nano-conductive compound may be a silver nanowire (AgNW), a carbon nanotube, or a graphene, etc.

Although not shown, the electrode EL may be variously shaped when viewed on a plane. The electrode EL may have a predetermined shape, such as a circle, oval, or polygon, or may be provided as a linearly extending wire. The electrode EL may be provided as a form that includes a portion having the predetermined shape and a wire extending thereto.

The second substrate SUB2 is provided on the first substrate SUB1 provided with the electrode EL. The second substrate SUB2 may cover the first substrate SUB1. Although termed a "substrate", the second substrate SUB2 may functions as a passivation that covers and protects the electrode EL and the first substrate SUB1.

The second substrate SUB2 may be transparent or opaque. The second substrate SUB2 may be flexible. The second substrate SUB2 may include one of the materials in the first substrate SUB1. The second substrate SUB2 may be formed of the same material as the first substrate SUB1 or a different material. The second substrate SUB2 may be composed of a flexible polymer insulator. The polymer insulator may include, in particular, a biostable material. The polymer insulator may include a fluorine-based polymer. The fluorine-based polymer may include at least one among polychlorotrifluoroethylene (PCTFE), perfluoro-2,2-dimethyl-1,3-dioxide (PDD), chlorotrifluoroethylene (CTFE), perfluoro-3-butenyl-vinylether (PBVE), perfluoropropylvinylether (PPVE), polytetrafluoroethylene (PTFE), polyvinylidenefluoride (PVDF), polyvinylfluoride (PVF), vinylidene fluoride (VDF), a PBVE-based homopolymer (Cytop™), and a copolymer including at least two thereof. The copolymer may include at least one among a copolymer of ethylene and CTFE (ECTFE), a copolymer of ethylene and TFE (ETFE), a copolymer of fluorinated ethylene and propylene (FEP), hexafluoropropylene (HFP), a copolymer of TFE and PPVE (PF A), a copolymer of TFE and PDD (Teflon™ AF), tetrafluoroethylene (TFE), and poly(TFE-co-HFP-co-VDF) (THV).

The first substrate SUB1 and the second substrate SUB2 are attached to each other at a contacting portion by thermal compression. At least a portion of an interface between the first substrate SUB1 and the second substrate SUB2 includes covalent bonds. Consequently, the attachment between the first substrate SUB1 and the second substrate SUB2 is stronger than attachments formed merely by intermolecular attractive forces (Van der Waals bonding).

In an electrode EL assembly of an embodiment of the inventive concept having the structure described above, the adhesion strength between the electrode EL and the first substrate SUB1 and the adhesion strength between the electrode EL and the second substrate SUB may be both excellent. Since the first substrate SUB1 and the second substrate SUB2 include materials having similar or identical physical properties, the adhesion strength between the first substrate SUB1 and the second substrate SUB2 may be superb when adhesion between the first substrate SUB1 and the second substrate SUB2 is carried out via thermal compression. In addition, according to an embodiment of the inventive concept, even though the materials in the first substrate SUB1 and the second substrate SUB2 may be insulating polymers, whereas the material for the electrode EL is formed of a different material to the first substrate SUB1 and the second substrate SUB2/, the adhesion strength between the substrates SUB1, SUB2 and the electrode EL is also superb. In an embodiment of the inventive concept, the electrode EL may be strongly attached directly onto the first substrate SUB1 without the presence of a separate adhesion layer for increasing the adhesion strength of the electrode EL.

The electrode assembly according to an embodiment of the inventive concept may further include a contact part CT to enhance contact between the electrode EL and a detection medium (solution, air, and/or bodily tissue, etc.). The contact part CT may be provided on the electrode EL. The contact part CT may form an electrode part ELP with the electrode EL.

The contact part CT may include a conductive material. In an embodiment of the inventive concept, the conductive material forming the contact part CT may be at least one of gold, silver, or platinum, and in particular, the conductive material may include gold.

The contact part CT may be provided porous or as a nanostructure. When the contact part CT is provided porous or as a nanostructure, it is easy to adjust the impedance of the electrode EL. When the contact part CT is provided porous or as a nanostructure, the surface area of the neural electrode EL per unit of surface area may increase, and thus the impedance of the neural electrode EL may decrease. Regarding the neural electrode EL, when the impedance decreases, electrical noise decreases, and consequently, the signal-to-noise ratio property in the neural electrode EL may improve.

The contact part CT may be provided on the electrode EL and directly contacts the electrode EL. The second substrate SUB2 may include a through-hole that exposes a top face of the electrode EL in a position at which the contact part CT is provided. After the through-hole is provided, the contact part CT may contact the electrode EL via the through-hole.

An electrode assembly having the structure described above may be manufactured by providing a first substrate SUB1 and a second substrate SUB2, plasma treating the first substrate SUB1, forming an electrode EL on the first substrate SUB1, and thermally compressing the first substrate SUB1 and the second substrate SUB2, with the electrode EL therebetween.

Figure 2A:
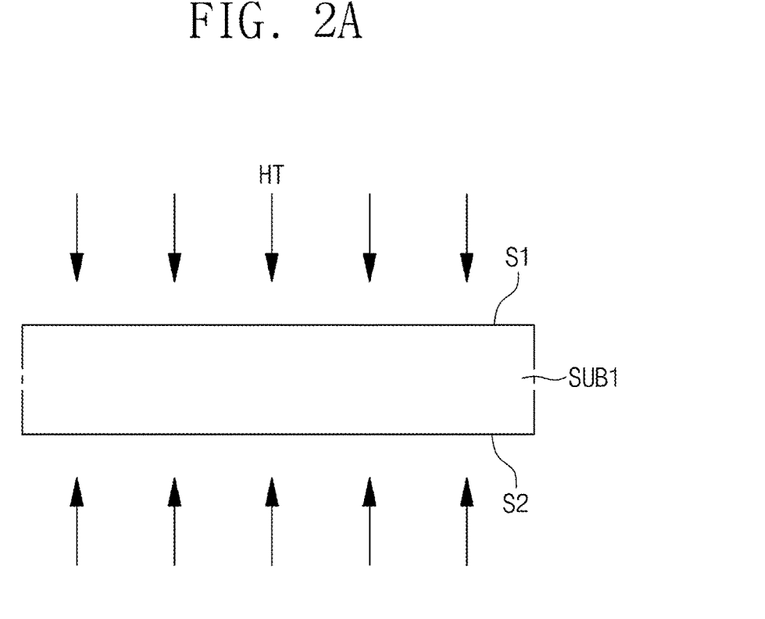
FIGS. 2A to 2Q are cross-sectional views sequentially illustrating a method for manufacturing an electrode assembly according to an embodiment of the inventive concept.

Hereinafter, a method for manufacturing the electrode assembly is described with reference to FIGS. 2A to 2Q. FIGS. 2A to 2Q are cross-sectional views sequentially illustrating a method for manufacturing an electrode assembly according to an embodiment of the inventive concept.

Referring to FIG. 2A, a first substrate SUB1 may be prepared, A heat treatment may is performed by applying predetermined heat HT to the first substrate SUB1. The first substrate SUB1 may be provided in the shape of a plate having a first face S1 and a second face S2. Stress generated inside the first substrate SUB1 may be relieved by the heat treatment. When the heat treatment is not performed, problems, such as shrinkage of the first substrate SUB1 during a thermal compression process, may occur in subsequent processes. Such problems may be eliminated by the heat treatment.

Figure 2B:
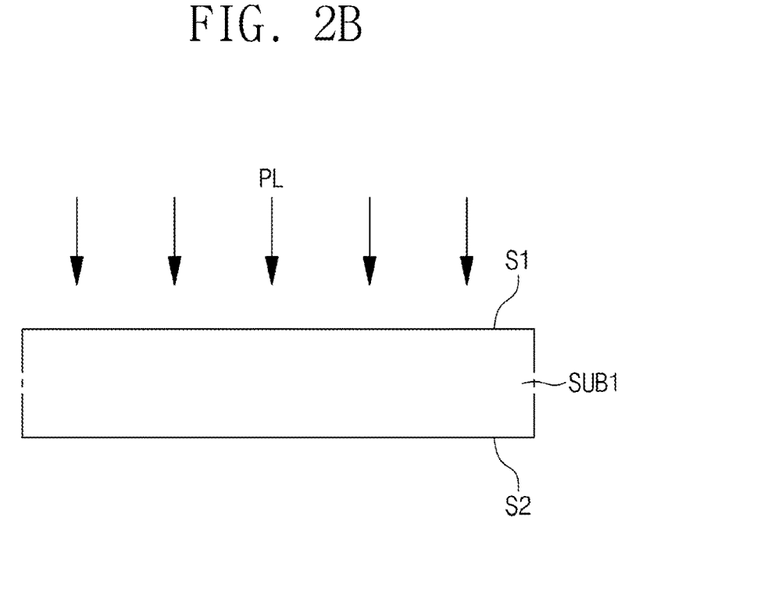

Referring to FIG. 2B, a plasma treatment may be performed by applying plasma PL to the first substrate SUB1. The plasma treatment may be performed on a face on which an electrode EL is to be subsequently formed. In an embodiment of the inventive concept, when the electrode EL is to be subsequently formed on the first face S1 among the two faces of the first substrate SUB1, the plasma treatment may be performed on the first face S1. RF plasma, DC plasma, remote plasma, magnetron plasma, etc. may be utilized in the plasma treatment. According to an embodiment of the inventive concept, RF magnetron plasma may be used. Argon, helium, oxygen, nitrogen, air, and/or carbon fluorides, etc. may be used as a plasma gas during the plasma treatment.

The first face S1 of the first substrate SUB1 may roughen, while at the same time, radicals may be formed on the first face S1 of the first substrate SUB1 by the plasma treatment. The adhesion strength with respect to the electrode EL and the other substrate (that is, the second substrate SUB2) in subsequent processes may change according to the roughness and presence, or lack thereof, of radicals on the first face S1. Fluorine-based polymers are chemically stable and thus have extremely weak adhesion strength with respect to metals and other materials. Adhesion between fluorine-based polymers may occur near or above the melting point. However, subsequent adhesion to the electrode EL and the other substrate (that is, the second substrate SUB2) is enhanced by using the plasma treatment as above to change the surface of the first substrate SUB1.

A wide range of process conditions may be set for the plasma treatment according to changes in the adhesion strength. For example, a wide range of values may be set for plasma power, plasma treatment time, or plasma gas pressure etc. according to changes in the adhesion strength.

The adhesion strength may be not proportional to plasma power, and may have a maximum value in a predetermined range. Plasma treatment time and plasma gas pressure may have an effect on the adhesion strength. When the plasma treatment time is insufficiently short or excessively long, the adhesion strength may be decreased. In an embodiment of the inventive concept, the plasma treatment time may be about 30 seconds to about 2 hours. In the case of the plasma gas pressure, although the adhesion strength increases as the pressure decreases, plasma generation is difficult if the pressure is too low. In an embodiment of the inventive concept, plasma treatment may be performed at a pressure of about 100 mTorr or lower, and may also be performed at a pressure of about 15 mTorr or lower.

Figure 2C:
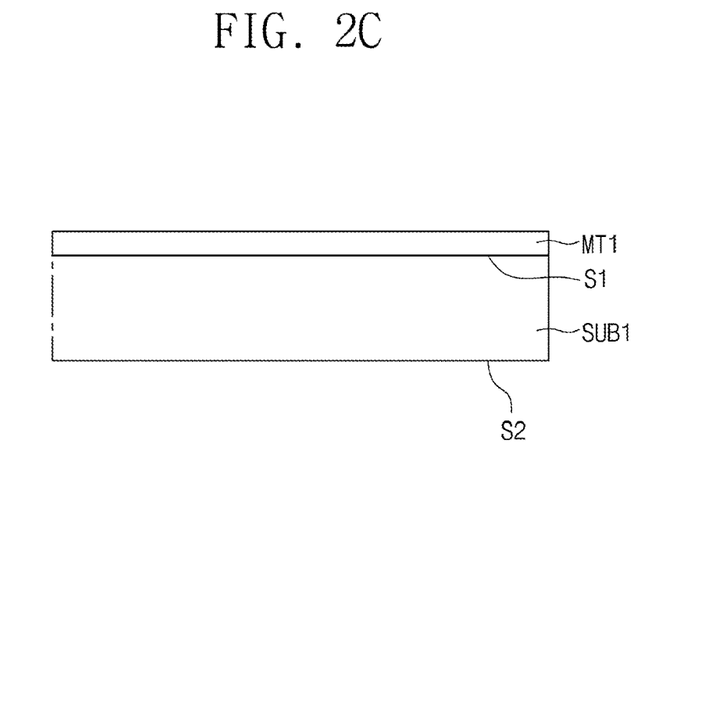

Referring to FIG. 2C, a first material layer MT1 may be formed on the top face of the plasma treated first substrate SUB1. The first material layer MT1 may be formed via thermal deposition or sputtering and the like. The first material layer MT1 may include electrode material. The first material layer MT1 may include a conductive material, and the conductive material may be at least one of gold, silver, or platinum. In an embodiment of the inventive concept, the conductive material may be gold.

However, as described above, the material of the conductive material is not limited thereto, and the conductive material may be composed of various materials according to the usage of the electrode assembly. For example, the electrode assembly may include various other conductive materials when used in a touch sensor and the like, and may include various metals, metal alloys, metal oxides, conductive polymers, or nano-conductive materials, etc. described above.

Figure 2D:
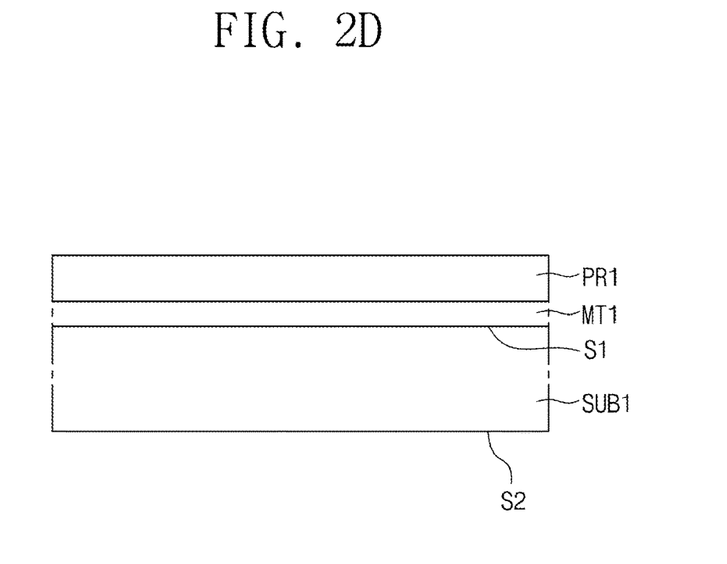

Referring to FIG. 2D, a first photosensitive film PR1 may be formed on the first material layer MT1. The first photosensitive film PR1 may be used to photolithographic patterning of the first material layer MT1.

Figure 2E:
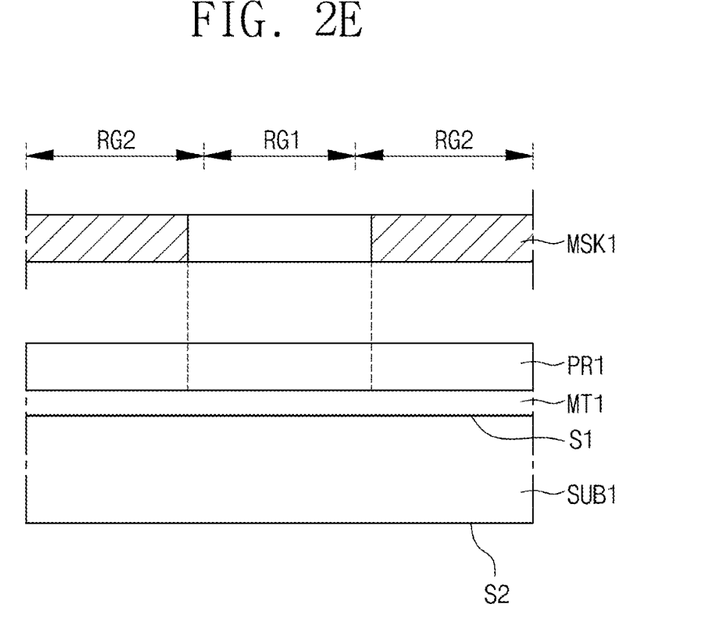

Referring to FIG. 2E, the first photosensitive film PR1 may be exposed to light. A first mask MSK1 may be used in the exposure. The first mask MSK1 may include a first region RG1 that transmits light and a second region RG2 that blocks light. The first region RG1 of first mask MSK1 may have a shape that corresponds to the shape of the electrode EL to be formed. Portions of the first photosensitive film PR1 may be exposed to light through the first region RG1 of the mask MSK1. The remaining portions of the first photosensitive film PR1 may be covered by the second region RG2 of the mask MSK1. The remaining portions of the first photosensitive film PR1 may be not exposed to light.

Figure 2F:
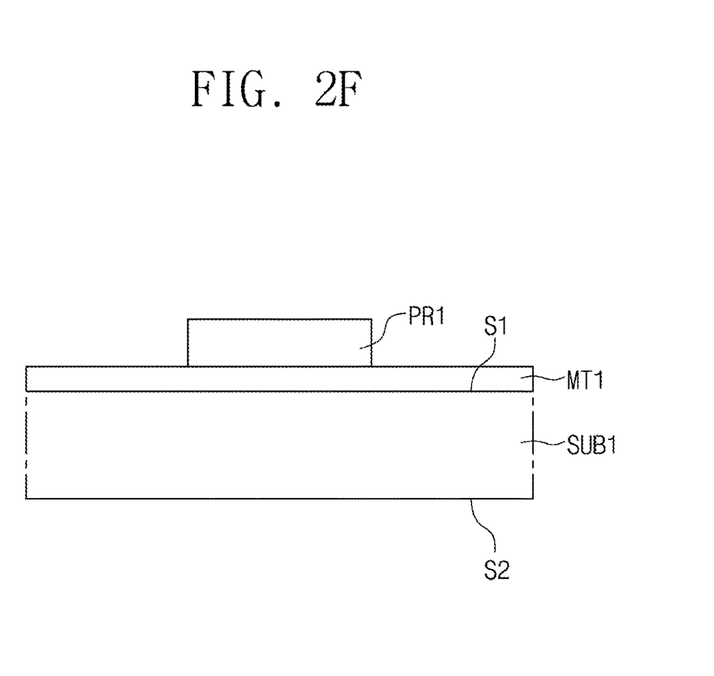

Referring to FIG. 2F, after the first photosensitive film PR1 may be developed. The first photosensitive film PR1 corresponding to the first region RG1 of first mask MSK1 may remain. The first photosensitive film PR1 corresponding to the second region RG2 of first mask MSK1 may be removed.

Here, in an embodiment of the inventive concept, although a photosensitive film may be used which involves a technique in which only portions not exposed to light are removed after development, embodiments of the inventive concept are not limited thereto. A photosensitive film may be used involving a technique in which portions exposed to light are removed after development.

Figure 2G:
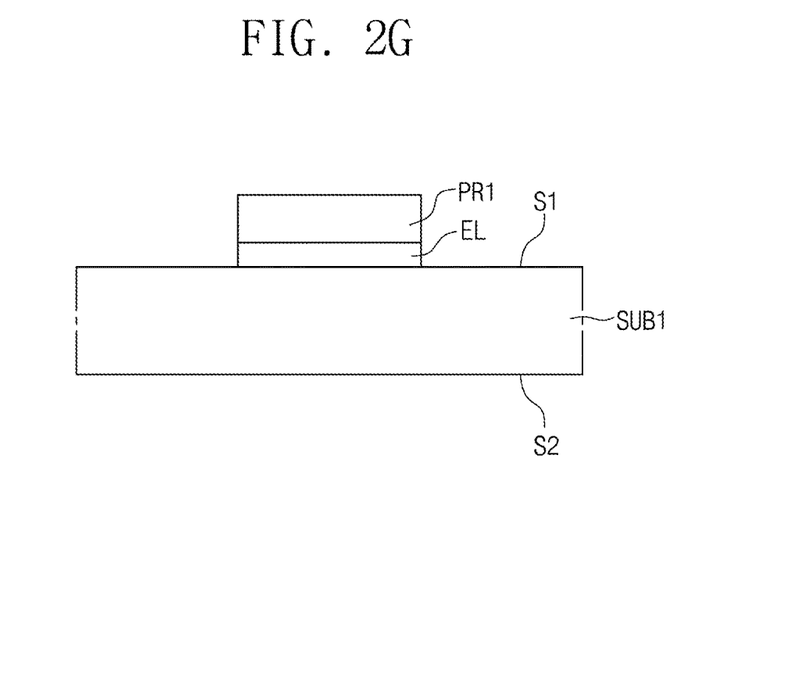

Referring to FIG. 2G, the electrode EL may be formed by patterning the first material layer MT1 using the remaining first photoresist film PR1 as a mask. The first material layer MT1 may be patterned using an appropriate method such as wet etching or dry etching. In an embodiment of the inventive concept, the first material layer MT1 may be wet patterned using an appropriate etching solution capable of etching the first material layer MT1. In another embodiment of the inventive concept, the first material layer MT1 may be patterned using a dry technique such as ion milling.

Figure 2H:
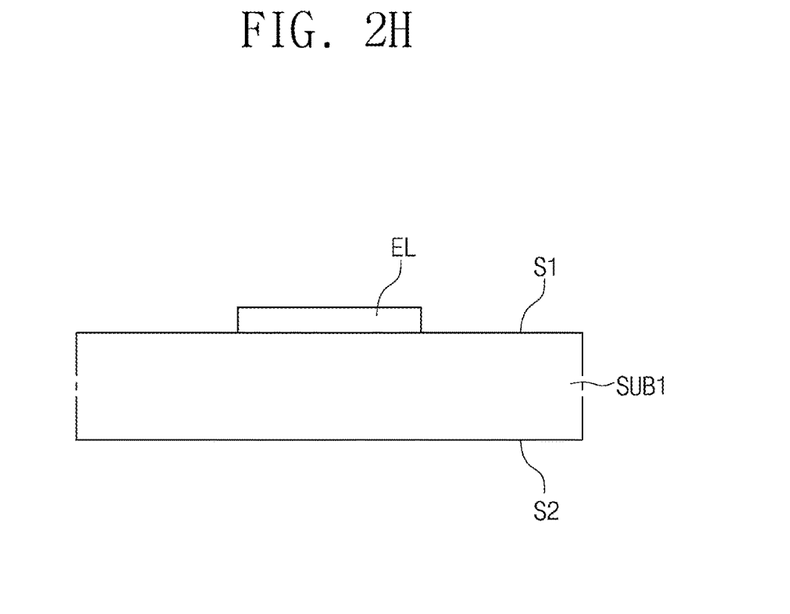

Referring to FIG. 2H, the remaining first photoresist film PR1 is removed.

Figure 2I:
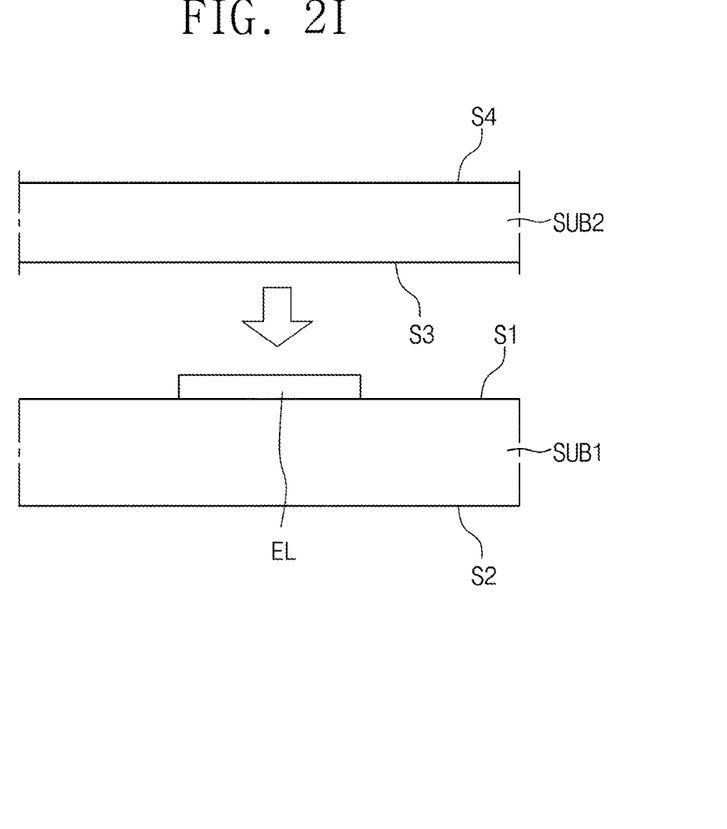

Referring to FIG. 2I, the second substrate SUB2 may be disposed on the first face S1 of the first substrate SUB1 on which is formed the electrode EL. The first and second substrates SUB1 and SUB2 may face each other. The second substrate SUB2 may passivate the electrode EL and the top face of the first substrate SUB1. The second substrate SUB2 may be provided in the shape of a plate. In this case, the second substrate SUB2 may have a third face S3 and a fourth face S4. The second substrate SUB2 may be thinner than the first substrate SUB1.

Like the first substrate SUB1, the second substrate SUB2 including a fluorine-based polymer is prepared. Although not shown, the second substrate SUB2 may be heat treated. The stress in or inside the second substrate SUB2 may be removed by the heat treatment. Moreover, plasma treatment may be performed on the second substrate SUB2. The plasma treatment may be performed on the second face S2 facing the first face S1 of the first substrate SUB1. The second face S2 of the first substrate SUB1 may come into contact with metal. If the third face S3 of the second substrate SUB2 is the face facing the first face S1 of the first substrate SUB1, the third face S3 may be prepared by being plasma treated. The fourth face S4 of the second substrate SUB2 may be the reverse face of the third face S3 of the second substrate SUB2.

Figure 2J:
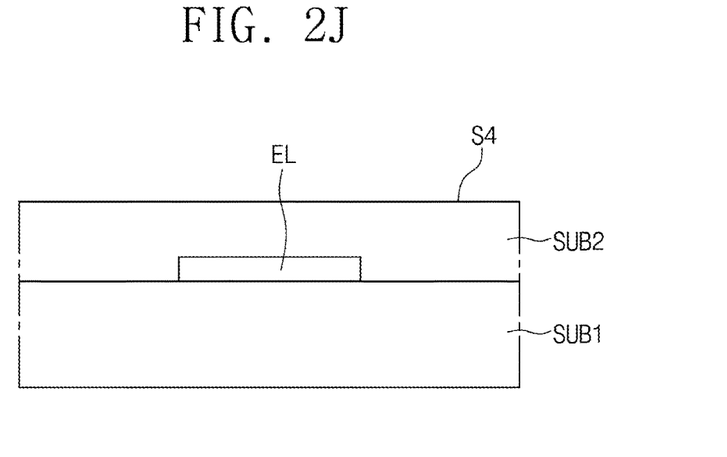

Referring to FIG. 2J, the heat treated and plasma treated second substrate SUB2 may be thermally compressed onto the first substrate SUB1. The temperature of the thermal compression of the first substrate SUB1 and the second substrate SUB2 may be set according to the material of the first substrate SUB1 and/or the second substrate SUB2. The temperature of the thermal compression may be set between the glass transition temperature and melting point of the first substrate SUB1 and/or the second substrate SUB2. Here, the thermal compression temperature when using the second substrate SUB2 to passivate the electrode EL may be reduced by plasma treating the second substrate SUB2. Fluorine-based polymers may require heat treatment at temperatures equal to or higher than the glass transition temperature due to having low adhesion strength. The adhesion of fluorine-based polymers is achieved near the melting point. When adhesion is achieved at such high temperatures, the electrode EL may be physically deformed. Thus, there may be a limitation in which precision manufacturing of the electrode EL. However, according to an embodiment of the inventive concept, since, by performing plasma treatment, the adhesion strength may be increased significantly in comparison to non-plasma treated fluorine-based polymers. The temperature of thermal compression may be set at a temperature below the glass transition temperature. For example, the temperature of thermal compression may be set between the glass transition temperature and the melting point of the first substrate SUB1 and/or the second substrate SUB2.

Through the thermal compression, the first substrate SUB1 may be attached to the electrode EL, the second substrate SUB2 may be attached to the electrode EL, and the first substrate SUB1 may be attached to the second substrate SUB2. Since the first face S1 of the first substrate SUB1 and the third face S3 of the second substrate SUB2 are plasma treated, not only are the surfaces thereof rough, but radicals are formed on portions thereof. When thermal compression is carried out in this state, bonding may be occur at highly rough portions, while at the same time, bonding (for example, covalent bonding) occurs amongst the radicals. Consequently, the adhesion strength significantly increases between the first substrate SUB1 and the electrode EL, between the second substrate SUB2 and the electrode EL, and between the first substrate SUB1 and the second substrate SUB2.

An electrode assembly may be formed through the process described above. The electrode assembly may be protected by the first substrate SUB1 and the second substrate SUB2. A contact part CT may be further formed in the electrode assembly. The contact part CT may enhance contact with a detection medium (solution, air, or bodily tissue, etc.) Hereinafter, formation of the contact part CT is described with reference to figures.

Figure 2K:
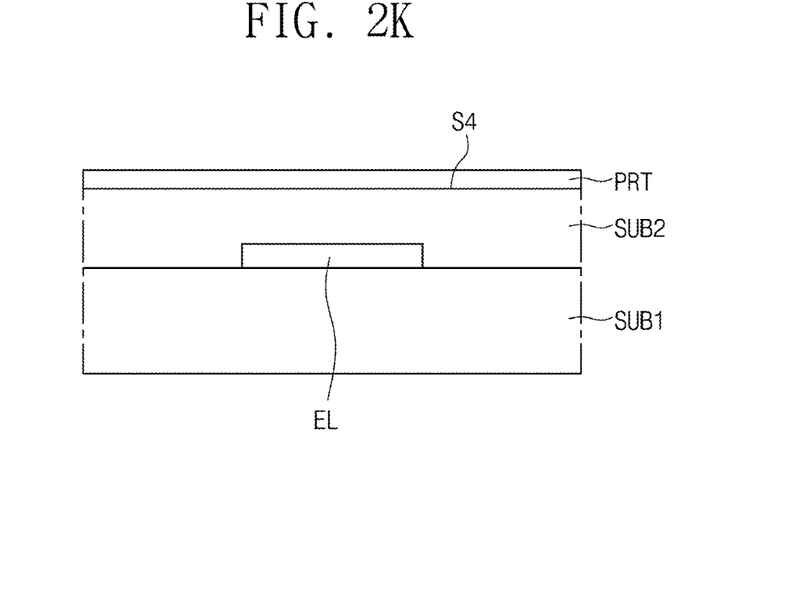

Referring to FIG. 2K, a protective layer PRT is formed on the fourth face S4 of the second substrate SUB2. The protective layer PRT may be formed using a sputtering method.

The protective layer PRT may be provided to protect the second substrate SUB2 from damage. The protective layer PRT may be removed after the processes are completed. The protective layer PRT may include a material that can protect portions of the second substrate SUB2 from etching. In an embodiment of the inventive concept, the protective layer PRT may include a metal or a metal alloy, and may include, for example, chrome and/or aluminum.

Figure 2L:
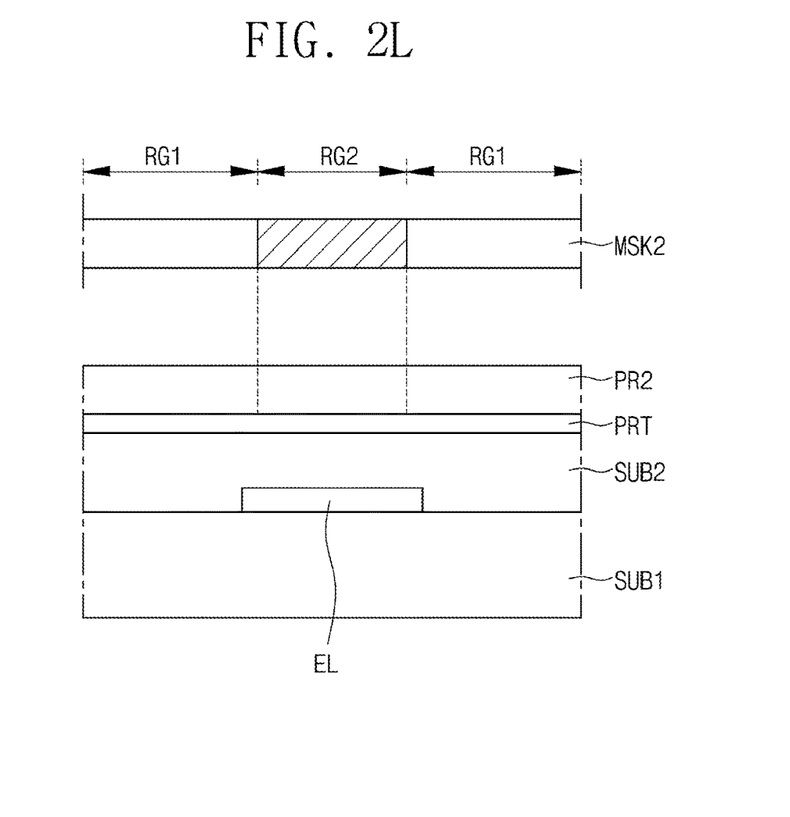

Referring to FIG. 2L, a second photosensitive film PR2 may formed on the protective layer PRT. The second photosensitive film PR2 is exposed to light. A second mask MSK2 may be used in the exposure. The second mask MSK2 may include a first region RG1 that transmits light and a second region RG2 that blocks light. The second region RG2 has a shape that corresponds to the shape of a through-hole to be formed. Portions of the second photosensitive film PR2 are exposed to light through the first region RG1. The remaining portions of the second photosensitive film PR2 are covered by the second region RG2 and thus are not exposed to light.

Figure 2M:
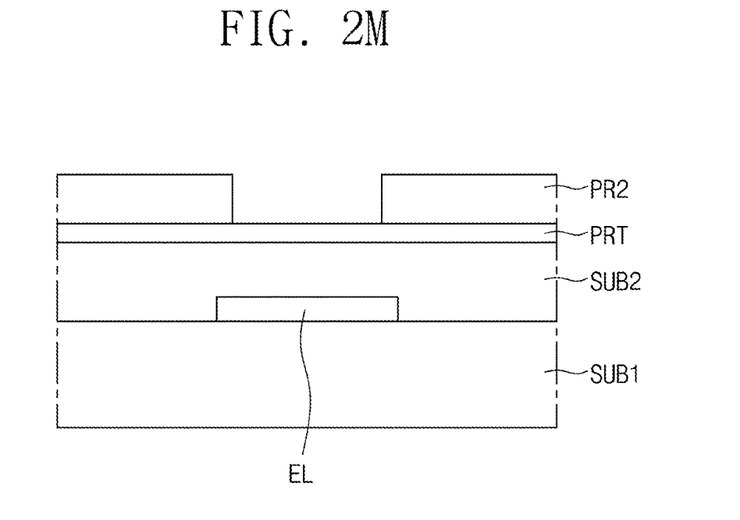

Referring to FIG. 2M, after the second photosensitive film PR2 may be developed. The second photosensitive film PR2 corresponding to the second region RG2 of the mask may be removed The second photosensitive film PR2 corresponding to the first region RG1 of the mask may remain. As in the first photosensitive film PR1, a photosensitive film involving a technique in which only portions not exposed to light are removed after development is used for the second photosensitive film PR2, but embodiments of the inventive concept are not limited thereto. Portions exposed to light of the second photosensitive film PR2 may be removed after development.

Figure 2N:
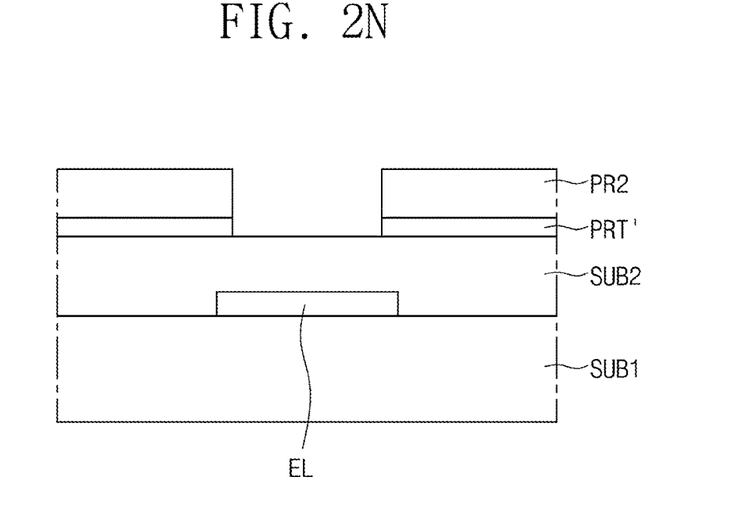

Referring to FIG. 2N, a protective pattern PRT' may be formed by patterning the protective film PRT using the remaining second photosensitive film PR2 as a mask. In an embodiment of the inventive concept, the protective layer PRT may be patterned via dry etching. A portion of the protective pattern PRT' is removed. A portion of the top face of the second substrate SUB2 may be exposed.

Figure 2O:
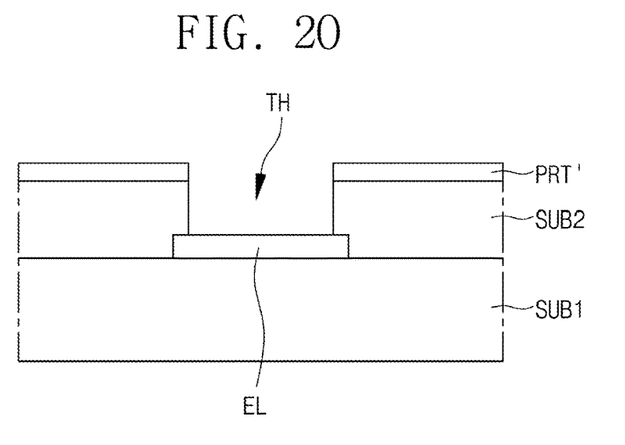

Referring to FIG. 2O, a through-hole TH may be formed by removing a portion of the second substrate SUB2 using the protective pattern PRT' as a mask. The through-hole TH may expose a portion of the top face of the electrode EL. Methods for forming the through-hole TH by etching a portion of the second substrate SUB2 are not particularly limited, and various methods may be used. In an embodiment of the inventive concept, a portion of the second substrate SUB2 may be dry etched using an oxygen plasma.

Figure 2P:
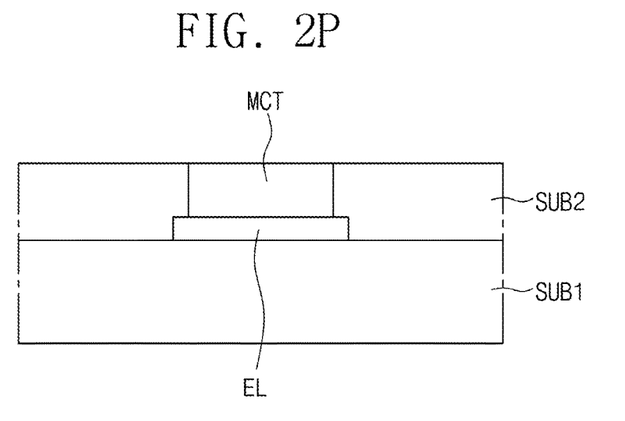
Figure 2Q:
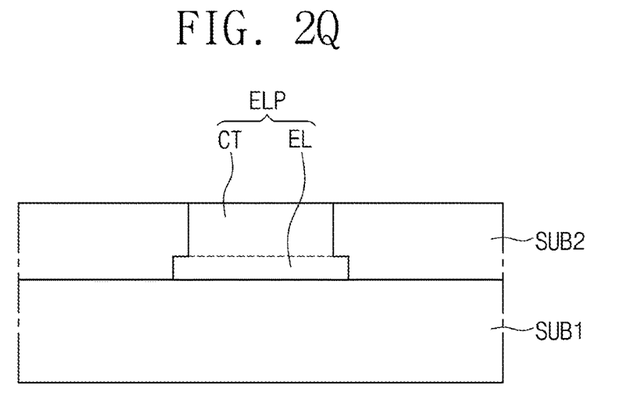

Referring to FIG. 2P, the protective pattern PRT' may be removed, and a preliminary contact part MCT may be formed in the through-hole TH. The preliminary contact part MCT may be formed using an electro-deposition technique. The preliminary contact part MCT may include a first metal and a second metal. The first metal and the second metal may be selected according to the ability thereof to dissolve in a predetermined etchant. In an example, the first metal may include silver (Ag), the second metal may include gold (Au), and the preliminary contact part MCT may include a silver-gold (Ag—Au) alloy layer. The silver (Ag) may not dissolve in nitric acid and the gold (Au). Silver (Ag) may dissolve in nitric acid. In another example, the preliminary contact part MCT may include a gold-platinum alloy layer. The gold-platinum alloy layer may be formed by selecting gold (Au), which dissolves in potassium iodide (KI), as the first metal and platinum (Pt), which does not dissolve in potassium iodide (KI), as the second metal.

Referring to FIG. 2Q, a contact part CT may be formed by selective removal of the first metal included in the preliminary contact part MCT. The contact part CT contains pores formed in portions in which the first metal has been removed. Accordingly, the contact part CT may be porous. The contact part CT may be formed, in particular, as a nanoporous metal structure including a plurality of nano-sized pores. Here, the first metal may be selectively dissolved by using a predetermined etchant. In an example, a nanoporous gold structure is formed by selectively dissolving the silver (Ag) in a silver-gold (Ag—Au) alloy layer using nitric acid as a silver etchant. In another example, a nanoporous platinum structure is formed by selectively dissolving gold (Au) using KI as a gold etchant. In addition, it is also possible to selectively remove the first metal by using an electrochemical etching technique to selectively remove a predetermined component. By forming the contact part CT as a porous material, the impedance of the electrode EL may be easily adjusted.

In an electrode assembly having the structure described above, a fluorine-based polymer-containing substrate may be attached to an electrode made of a conductive material, such as a metal, without using a separate adhesive or adhesive metal. Accordingly, an electrode assembly may be stably realized, for an extended period of time, inside or outside a living body, without the use of a corrosion-generating element, such as an adhesive or an adhesive metal.

Figure 3:
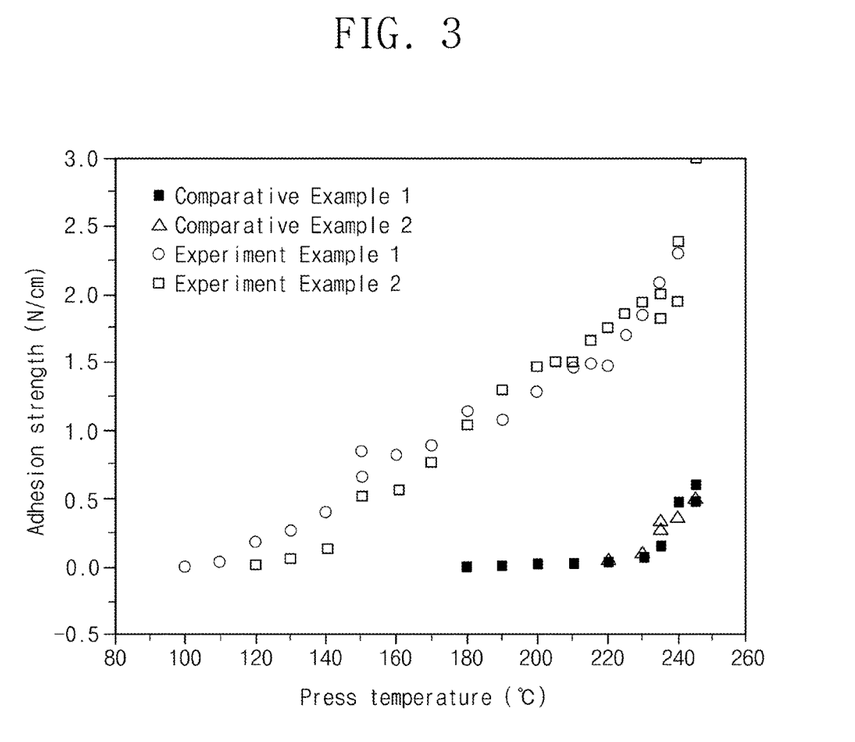
FIG. 3 is a graph illustrating the adhesion strength between substrates and metals according to thermal compression temperature, in a manufacturing process for an electrode assembly according to an embodiment of the inventive concept.

FIG. 3 is a graph illustrating the adhesion strength between substrates and metals according to thermal compression temperature, in a manufacturing process for an electrode assembly according to an embodiment of the inventive concept.

In the graph in FIG. 3, Comparative Example 1 and Comparative Example 2 illustrate the adhesion strength between a fluorine-based polymer-containing substrate and a gold electrode according to thermal compression temperature, in cases in which plasma treatment has not been performed on the substrate. Experiment Examples 1 and 2 illustrate the adhesion strength between a fluorine-based polymer-containing substrate and a gold electrode according to thermal compression temperature, in cases in which plasma treatment has been performed on the substrate. Here, the gas used in the plasma treatment of Experiment Example 1 is oxygen, and the gas used in the plasma treatment of Experiment Example 2 is argon.

Referring to FIG. 3, in Comparative Examples 1 and 2, attachment of the substrate to the electrode is not substantially achieved at temperatures below about 170 degrees, and an adhesion strength of about 0 to 0.7 N/cm is exhibited when compression is carried out at a temperature of about 170 to 250 degrees. In contrast, in Experiment Examples 1 and 2, an adhesion strength of about 0 to 3.0 N/cm is exhibited, independent of plasma gas, when compression is carried out at a temperature of about 100 to 250 degrees. In particular, in Experiment Examples 1 and 2, an adhesion strength of about 1.0 N/cm is exhibited even at a relatively low temperature of about 100 to 170 degrees, and an adhesion strength of at least about 1.0 N/cm is exhibited at temperatures at or above about 180 degrees. This corresponds to an adhesion strength that is higher than that of 3M Scotch Tape (810D), which exhibits adhesion strength of about 0.8 to 1.0 N/cm.

As described above, according to an embodiment of the inventive concept, it is observed that since plasma treatment is performed on a fluorine-based polymer substrate, the adhesion strength between the substrate and an electrode is significantly increased even when thermal compression is carried out at a low temperature. Moreover, according to an embodiment of the inventive concept, it is observed that the adhesion strength between the substrate and the electrode is significantly increased independent of the type of plasma gas used. When the thermal compression temperature is significantly lowered in this manner, thermal deformation of the substrate and electrode may be minimized.

Since the electrode assembly manufactured using the above method does not include delamination-causing factors such as metals used as adhesives, for instance, Cr or Ti, the durability of the adhesion between the electrode and the substrate is significantly enhanced.

Polyimide, polydimethylsiloxane (PDMS), liquid crystal polymers, and/or epoxy-based negative photoresists (SU-8), etc. have been used in electrode assemblies as materials for first and second substrates (that is, a substrate and a passivation covering the substrate), and Au and Pt have usually been used as electrode materials. Here, the respective materials used for the first substrate and the second substrate may be the same of different. However, electrode materials such as Au and Pt may be chemically stable. Since the bonding strength between electrode materials and polymers used in the substrate is inherently extremely weak, there is a limitation in that separation easily occurs. Accordingly, metals, such as Cr or Ti may be used as adhesive layers between Au or Pt and polymer substrates in order to increase the adhesion strength between metals, such as Au and Pt, and polymers. The metals, such as Cr or Ti may have relatively good adhesion strength with polymers. However, the moisture absorbing property of the polymers accelerate weakening of the adhesion strength between the polymer substrate and the adhesion layer, and Cr or Ti, when used for extended periods of time, are subject to corrosion or weakened adhesion strength caused by bodily fluids, sweat, moisture, repeated mechanical stimulation, etc. Thus, ultimately, there is a limitation in which delamination of Au or Pt from the polymer substrate occurs. In other words, when exposed inside the body for an extended period of time, the adhesive layer made of chrome or titanium and the like may dissolve inside the body, and thereby be lost. In particular, sodium ions (Na+) or potassium ions (K+) are present inside the body. Reactions between the sodium ions or potassium ions and the metals in the adhesive layer may result in loss of the adhesive layer. Such loss of the adhesive layer causes deintercalation of the electrode EL, and ultimately leads to malfunction of elements adopting the electrode EL.

In contrast, according to an embodiment of the inventive concept, since the adhesion strength between a first substrate and a second substrate, between the first substrate and an electrode, and between the electrode and the second substrate is significantly increased in an electrode assembly, delamination of the electrode from a polymer substrate is reduced or prevented, even when an adhesive layer is not provided.

Accordingly, embodiments of the inventive concept may be used in various applications requiring long implant stability, such as bio-implantable and bio-attachable electrodes, in particular, neural electrodes. Here, the neural electrode may be used in the fields of in vivo or in vitro neural interfaces. The neural electrode may be used to provide electrical stimulation to nerves or to measure or record nerve signals. Moreover, having excellent durability against strong acids, strong bases, and various solvents, the electrode assembly manufactured using the above method may be utilized in various elements requiring extreme conditions. For example, the electrode assembly may be applied as an electrode in a chemical sensor.

According to an embodiment of the inventive concept, an electrode assembly having increased adhesion strength between a substrate and an electrode, and a method for manufacturing the same are provided.

Although the exemplary embodiments of the present invention have been described, it is understood that the present invention should not be limited to these exemplary embodiments but various changes and modifications can be made by one with ordinary skill or knowledge in the art within the spirit and scope of the present invention as hereinafter claimed.

Therefore, the technical scope of the present invention is not limited to the detailed description of the specification, but rather, should only be defined by the scope of the claims.

What is claimed is:

1. A method for manufacturing an electrode assembly, the method comprising:
    providing a first substrate and a second substrate;
    plasma treating the first substrate;
    forming an electrode on the first substrate;
    thermally compressing the first substrate and the second substrate, with the electrode therebetween; and
    patterning a portion of the second substrate to thereby form a through-hole that exposes a portion of a top face of the electrode,
    wherein each of the first substrate and the second substrate includes a fluorine-based polymer.

2. The method of claim 1, wherein the patterning of a portion of the second substrate comprises:
    forming a protective layer on the top face of the second substrate;
    patterning the protective layer to removing a first region;
    etching the second substrate corresponding to a patterned and removed portion of the protective layer; and
    removing the protective layer.

3. The method of claim 2, further comprising forming a contact part in the through-hole, wherein the contact part is composed of a porous conductive material.

4. The method of claim 3, wherein the contact part is formed by using an electro-deposition method.

5. An electrode assembly comprising:
a first substrate;
an electrode provided on the first substrate;
a second substrate which is thermally compressed to the first substrate, with the electrode therebetween, wherein each of the first substrate and the second substrate includes a fluorine-based polymer; and
a contact part provided on the electrode, wherein the contact part is porous.

6. The electrode assembly of claim 5, wherein the fluorine-based polymer comprises at least one among polychlorotrifluoroethylene (PCTFE), perfluoro-2,2-dimethyl-1,3-dioxide (PDD), chlorotrifluoroethylene (CTFE), perfluoro-3-butenyl-vinylether (PBVE), perfluoropropylvinylether (PPVE), polytetrafluoroethylene (PTFE), polyvinylidenefluoride (PVDF), polyvinylfluoride (PVF), vinylidene fluoride (VDF), a PBVE-based homopolymer (Cytop™), and a copolymer including at least two thereof.

7. The electrode assembly of claim 6, wherein the copolymer is a copolymer of ethylene and CTFE (ECTFE), a copolymer of ethylene and TFE (ETFE), a copolymer of fluorinated ethylene and propylene (FEP), hexafluoropropylene (HFP), a copolymer of TFE and PPVE (PFA), a copolymer of TFE and PDD (Teflon™ AF), tetrafluoroethylene (TFE), or poly(TFE-co-HFP-co-VDF) (THV).

8. The electrode assembly of claim 5, wherein
the second substrate comprises a through-hole that exposes a portion of a top face of the electrode; and
the contact part is provided in the through-hole.

9. The electrode assembly of claim 5, wherein the chemical bonding comprises a covalent bonding formed by the first radical and the second radical.

* * * * *